United States Patent [19]

Froning et al.

[11] Patent Number: 4,571,243
[45] Date of Patent: Feb. 18, 1986

[54] NEEDLE GUIDANCE SYSTEM

[75] Inventors: Edward C. Froning, P.O. Box 1768, Rancho Santa Fe, Calif. 92067; Gregory S. Graham, Ventura, Calif.

[73] Assignee: Edward C. Froning, Santa Fe, Calif.

[21] Appl. No.: 495,664

[22] Filed: May 18, 1983

[51] Int. Cl.[4] ............................................. A61M 5/00
[52] U.S. Cl. ..................................... 604/116; 604/51; 128/303 B; 248/206.5
[58] Field of Search .............. 604/116, 51; 128/303 B, 128/DIG. 26; 211/DIG. 1; 248/206.5

[56] References Cited

U.S. PATENT DOCUMENTS

| | | | |
|---|---|---|---|
| 3,196,875 | 7/1965 | Pfeiffer | 128/303 B |
| 3,209,729 | 10/1965 | Zedaker | 248/206.5 |
| 3,941,127 | 3/1976 | Froning | 604/51 |
| 3,964,480 | 6/1976 | Froning | 128/303 B |
| 4,447,238 | 5/1984 | Eldridge | 128/DIG. 26 |

*Primary Examiner*—C. Fred Rosenbaum
*Assistant Examiner*—Mark Rooney
*Attorney, Agent, or Firm*—Julian Caplan

[57] ABSTRACT

System for stereotaxic lateral extradural disc puncture has a frame fitting over the patient which provides for proper location of the cannula of the needle. The frame has a pair of right-angle members. A lower bridge frame extends horizontally and is clipped to the vertical legs of the right angle members by magnetic clips. A bridge clip fits onto the lower bridge frame and is longitudinally slidable thereon. The stem of the cannula guide slides vertically in the bridge clip. A half-channel on the top of the stem comprises the cannula guide and a bead chain fixed near the half-channel insures that the stem is vertical. Forward and rear heading guide supports are magnetically attached to the horizontal legs of the right-angle members. These supports hold magnetic strips by which a transverse disc overlay strip is held in place. A second bead chain depends from the forward end of the disc overlay strip to locate the proper alignment of the point of the cannula.

6 Claims, 9 Drawing Figures

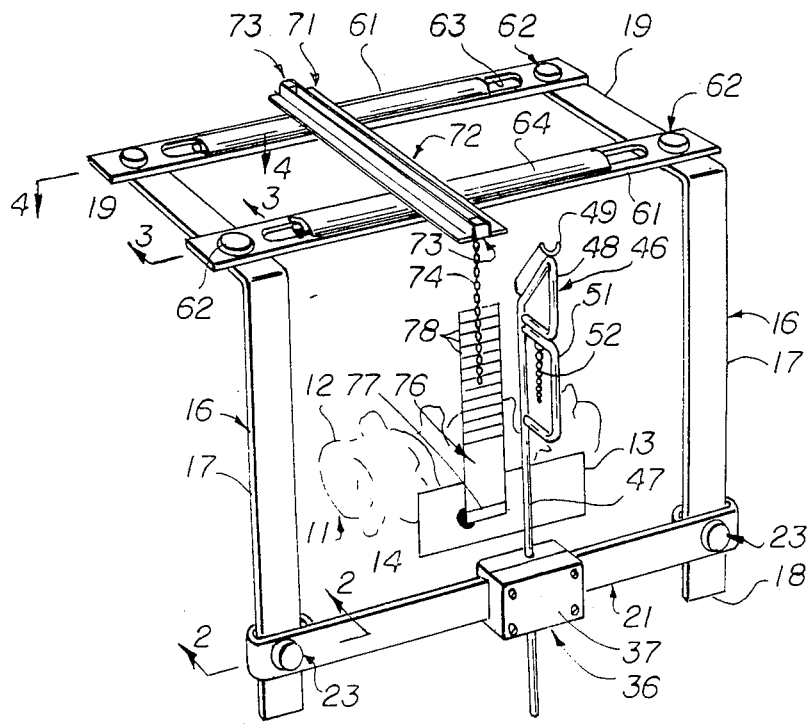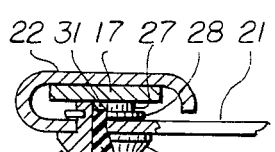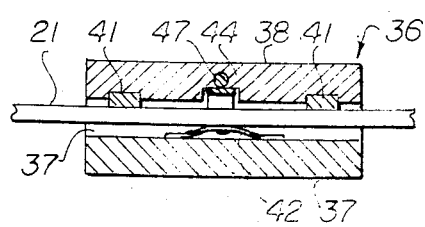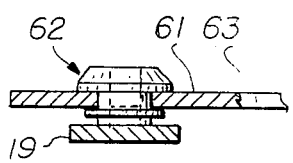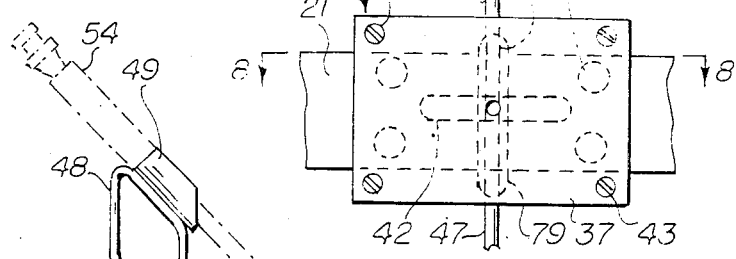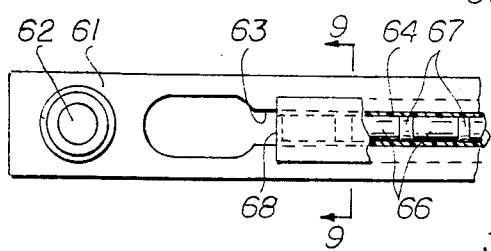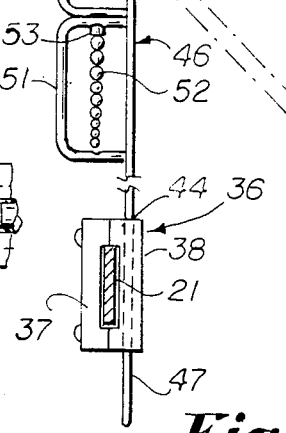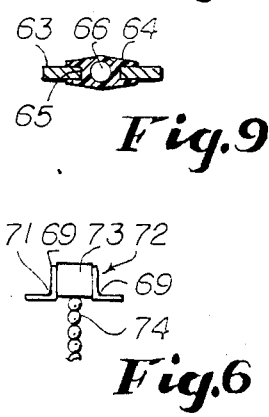

NEEDLE GUIDANCE SYSTEM

This invention relates to a new and improved system for stereotaxic extradural disc puncture and constitutes an improvement upon prior U.S. Pat. No. 3,941,927, to which reference is made for an understanding of the background and general objectives of the system.

The present invention comprises an improvement on the system shown in said U.S. Pat. No. 3,941,127 in a number of respects. One improvement is the fact that the construction of the devices hereinafter described is such that manipulation of the parts in order to place them in proper position of adjustment requires less attention from the surgeon or his assistant, speeding the operation and allowing the surgeon to concentrate upon the operation itself, rather than upon the adjustment of the equipment.

Another improvement over prior constructions is that safeguards are built into the equipment to insure proper vertical and horizontal alignment of the point of skin puncture by the cannula so as to reduce the possibility of improper location of the disc puncture needle.

Another feature of the invention is the fact that the equipment is able to be readily cleaned and/or sterilized.

Other objects of the present invention will become apparent upon reading the following specification and referring to the accompanying drawings in which similar characters of reference represent corresponding parts in each of the several views.

IN THE DRAWINGS

FIG. 1 is a perspective view showing the system in place relative to the spine of the patient;

FIGS. 2, 3 and 4 are, respectively, fragmentary sectional views taken substantially along the lines 2—2, 3—3 and 4—4 of FIG. 1;

FIG. 5 is an end elevational view of the cannula guide and associated parts;

FIG. 6 is a fragmentary side elevational view showing the attachment of a bead chain to the transverse disc overlay strip;

FIG. 7 is an enlarged elevational view of the center bridge clip;

FIG. 8 is a sectional view taken substantially along the line 8—8 of FIG. 7.

FIG. 9 is a sectional view taken substantially along line 9—9 of FIG. 4.

In U.S. Pat. No. 3,941,127 is disclosed a pre-operative radiography procedure which determines upon an X-ray film the depth within the body of the patient of the disc to be punctured. This film is exposed while the patient is lying on his side. Prior to the operation, the surgeon calculates the site of skin puncture for an angled needle approach to the disc at an angle of 45° downwardly and rearwardly. During the operation, the patient is positioned in the same location as the pre-operative radiograph upon a radiolucent table top and the torso is strapped or retained to prevent drift out of lateral position. Further details of the pre-operative and operative techniques are set forth in said U.S. Pat. No. 3,941,127 and are not repeated herein.

In FIG. 1 is shown the outline of a portion of the spine 11 and the location of disc 12 which is to be punctured. At the outset, an adhesive strip 13 is applied to the skin at the level of the spine 11 and a radiographic opaque marker 14 is applied immediately in alignment with the disc 12 at the center line of the spine 11. Thereupon, the apparatus hereinafter described is placed in position.

Left and right right-angled frame members 16 are provided, each having a vertical stretch 17 with a foot 18 at the bottom which rests on the table and a horizontal stretch 19. Extending longitudinally of the patient near the table is lower bridge frame 21, which is a strip formed with a bend 22 at either end which surrounds one of the vertical stretches 17 so that the frame 21 may be raised or lowered relative to the frames 16.

Adjustment of the strip 21 is made so that the strip is perfectly horizontal. Clip 23 consists of a cup 24 having an enlarged head 26 on the forward side of strip 21 and a reduced diameter hollow stem 27 which extends through a hole in strip 21 and is held in place by spring clip retainer 28. Within the hollow of stem 27 is a magnet 29 having a nonmagnetic plug 31 of aluminum or similar material which prevents damage to the magnet when the clip 23 is sterilized. As is apparent particularly from FIG. 2, the strip 21 may be raised and lowered relative to vertical stretch 17, but the magnet 29 holds the parts in position against unintentional dislodgment.

Slidable along the lower bridge frame member 21 is bridge 36. As best shown in FIGS. 7 and 8, clip 36 may be constructed of a front member 37 and a rear member 38 held together by screws 43. The mating surfaces of members 37, 38 are cut away to provide an opening 39 which is wider than the thickness of lower bridge frame member 21. Sliders 41 which may be Teflon discs, are attached to rear members 38 and bear against the back of strip 21. A leaf spring, or other resilient member, 42 is attached to front member 37 and bears against the front of strip 21. Hence, the bridge clip 36 may be moved horizontally longitudinally of the patient, but is held in position of adjustment against unintentional dislodgment by spring 42. Extending through rear member 36 is a vertical hole 44 for the stem 47 of cannula guide 46. Cannula stem 47 may be moved vertically and retained in position and against unintentional dislodgment by leaf spring or other resilient member 79. Spring 79 is contained in a pocket in rear member 38 and bears against the stem of Cannula 47 and surface member 37.

Cannula guide 46 has a vertical stem 47 of wire or other suitable material which is formed into a triangular support 48 at the top to which is secured a half channel 49 disposed at an angle of 45° downwardly and toward the patient relative to the stem 47. Below the support 48, the stem 47 is provided with a frame 51 from the top of which is suspended a chain 52 by an attachment 53. Chain 52 serves as an indicator to insure that the stem 47 is vertical. As is described in said U.S. Pat. No. 3,941,127, a cannula-needle system 54 is placed in the channel 49 which serves as a guide to insure that the point of the cannula enters the skin of the patient at a 45° angle.

Extending longitudinally at the top are front and rear guide supports 61. At either end supports 61 are apertured for clips 62 similar to clips 23. Thus, the supports 61 may be adjusted in position relative to the horizontal stretches 19 of the right angular frame member 16 and, once adjusted, the magnets within the clip 62 hold the supports 61 in position. Each support 61 is formed with a longitudinal slot 63 into which a tube 64 is mechanically held, or otherwise secured. Tube 64 is filled with a plurality of magnets 66 spaced apart by non-magnetic spacers 67. The ends of the tube are filled with plugs 68 to protect the interior. Tube 64 is of a flexible material and is formed with longitudinal grooves 65 to receive the margins of slot 63 of support 61.

Extending transversely of the supports 61 is disc overlay strip 71. As shown particularly in FIG. 6, strip 71 is formed with angles 69 spaced apart at each end with spacers to form a channel 72 which is open. During the operation, because of the opaque material of the side angles 69 of the channel 72, a sharp parallel line appears on the fluorescent screen used during the operation and this shadow should overlay the disc 12. To the forward end of strip 71 is attached second plumb bob chain 74.

A ruler 76 is attached by adhesive to the torso of the patient. Ruler 76 has a zero marking 77 which is aligned with the center of the marker 14. Ruler 76 has a plurality of height markings 78. The chain 74 depends in proximity to the upper end of the ruler 76. Hence, the surgeon raises and lowers the stem 47 until the distal of the cannula is directed at the intersection of the chain 74 and the particular marker 78 which has been selected from the preoperative radiographic film as the precise point for puncture of the skin of the patient.

What is claimed is:

1. A needle guide of the type having a pair of right-angle supports having vertical and horizontal members, a lower bridge frame extending horizontally across both said vertical members, first clips fixed to opposite ends of said lower bridge frame engaging said vertical members, a bridge clip adjustably slidable along said lower bridge frame, a cannula guide having a stem vertically slidable in said bridge clip and having a downward-inward slanted channel, a forward and a rearward horizontal longitudinal heading guide extending across both said horizontal members, second clips fixed to opposite ends of said heating guides engaging said horizontal members, a disc overlay extending transversely to said heading guides, disc overlay holding means holding said disc overlay in engagement with said heading guides and plumb means depending from the forward end of said disc overlay, the improvement which comprises said right angle supports being of magnetizable material, said first clips each comprising a hollow first stem passing through said lower bridge frame, a first magnet in said first stem magnetically engageable with said vertical member and means securing said first stem fixed to said lower bridge frame, said second clips each comprising a hollow second stem passing through one said heading guide, a second magnet in said second stem magnetically engageable with said horizontal members and means securing said second stem fixed to said heading guide.

2. A guide according to claim 1 in which said magnetic means comprises a series of magnets distributed longitudinally of said heading guides, said said disc overlay being engageable with any one of the said series of magnets.

3. A guide according to claim 1 in which said disc overlay contains relatively narrow strips of radiopaque material.

4. A guide according to claim 1 in which said bridge clip is formed with a longitudinal opening within which said bridge frame fits and resilient means in said opening bearing against said bridge frame.

5. A guide according to claim 1 in which said cannula guide has means directly below said channel supporting a second plumb means indicating when said stem is vertical.

6. A guide according to claim 1 which further comprises a radiopaque marker, means to attach said marker to the skin of a patient at the level of and opposite a spinal disc to be punctured, a ruler having a lower zero line to be placed at the level of said marker and a plurality of vertically spaced height markings, and means to attach said ruler to the skin of the patient, said plumb means being located in proximity to said ruler.

* * * * *